US00PP08955P

United States Patent [19]

Wilson

[11] Patent Number: Plant 8,955

[45] Date of Patent: Oct. 25, 1994

[54] "EARLY ROSA" PLUM TREE

[76] Inventor: David A. Wilson, 10735 E. Mission Ave., Le Grand, Calif. 95333

[21] Appl. No.: 148,971

[22] Filed: Nov. 2, 1993

[51] Int. Cl.[5] ..... A01H 5/00
[52] U.S. Cl. ..... Plt./38.1
[58] Field of Search ..... Plt. 38.1

*Primary Examiner*—James R. Feyrer
*Attorney, Agent, or Firm*—Worrel & Worrel

[57] ABSTRACT

A new and distinct variety of plum tree which is somewhat remotely similar to the "Santa Rosa"]plum tree (unpatented), but from which it is distinguished by producing fruit which are mature for harvesting and shipment approximately seven days to ten days prior to the fruit produced by the "Santa Rosa" plum tree and wherein the fruit is of an excellent quality having a sweet, rich flavor, a bright cherry red to dark purple skin coloration and a moderately firm clingstone flesh.

1 Drawing Sheet

BACKGROUND OF THE NEW VARIETY

The present invention relates to a new and distinct variety of plum tree which will hereinafter be denominated varietally as "Early Rosa" plum tree and, more particularly, to a plum tree which produces clingstone fruit, which are mature for commercial harvesting and shipment approximately June 14 to June 19 in the northern San Joaquin Valley of California, having a sweet, rich flavor, moderately firm flesh and bright cherry red to dark purple skin coloration.

The "Santa Rosa" type plum has over a broad expanse of years developed a significant and seemingly permanent share of the fresh plum market. Due to its durability in the marketplace, there has been a well recognized and more or less continuous effort to develop new varieties of plum trees of the "Santa Rosa" type which bear fruit having enhanced, commercially appealing attributes including ripening dates which expand the market season for fresh "Santa Rosa" type plums beyond that which has previously been available. These efforts have not been consistently successful. The new variety of the present invention is believed to succeed admirably in these respects.

ORIGIN AND ASEXUAL REPRODUCTION OF THE NEW VARIETY

The present variety of plum tree hereof was discovered in June, 1987 by the inventor in his orchard located near Le Grand in the northern San Joaquin Valley of California. The inventor discovered the new variety as a mutation of the "Late Santa Rosa" plum tree (unpatented). The inventor asexually reproduced the new variety in June, 1987 at Bright's Nursery in Le Grand, Calif., by placing leaf axillary buds on root stock using "T" grafts.

SUMMARY OF THE NEW VARIETY

The "Early Rosa" plum tree is characterized by producing a clingstone fruit which have a bright cherry red to a dark purple skin coloration and which are ripe for commercial harvesting and shipment approximately June 14 to June 19 in the northern San Joaquin Valley of California, or approximately seven to ten days prior to the "Santa Rosa" plum tree (unpatented). The new variety is most closely similar to the "Santa Rosa" plum tree, but is distinguished therefrom by the aforementioned ripening date as well as by other characteristics.

The fruit is clingstone, having a sweet, rich flavor and a bright cherry red to dark purple skin coloration. The new variety has the potential for expanding the "Santa Rosa" type plum market by ripening earlier in the season than any commercially viable "Santa Rosa" type plum.

BRIEF DESCRIPTION OF THE DRAWING

The accompanying drawing is a color photograph showing fruit of the new variety including a first disposed to reveal the base end thereof; a second in side elevation showing the suture; a third showing the apex end thereof; a fourth in side elevation; and a fifth sectioned and laid open to display one section with the stone left in place and the other section with the pit cavity exposed; a stone of the new variety; and representative foliage thereof.

DETAILED DESCRIPTION

Referring more specifically to the pomological details of this new and distinct variety of plum tree, the following has been observed under the ecological conditions prevailing at the orchard of origin which is located near Le Grand in the northern San Joaquin Valley of California. All major color code designations are by reference to the *Dictionary of Color,* by Maerz and Paul, First Edition, 1930. Common color designations are also occasionally employed.

TREE

Generally: Hardy and productive with 91.44 cm (36 inches) to 121.92 cm (48 inches) of new growth in the upper portion of the asexually reproduced trees each season.

*Vigor.*—Vigorous.

*Form.*—Upright to upright-spreading.

*Figure.*—Trained to a standard vase shaped system.

*Productivity.*—Productive under climatic conditions typical for the San Joaquin Valley of California.

*Regularity of bearing.*—Regular.

Trunk:

*Size.*—Average thickness.

*Surface texture.*—Relatively rough with moderate scarfskin.

*Color.*—Medium grey-brown (8-H-9 Rembrandt Brown).

*Lenticels.*—Numbers — Numerous. Size — Large, wide and oval. From 6 mm (0.2362 inches) to 12 mm (0.4724 inches) in width.

Branches:

*Size.*—Medium thickness.

*Surface texture.*—Relatively smooth.

*Color.*—One year or older wood — Medium brown (7-H-11 Casserole Brown) to a brown-green (15-E-10 Olive Wood Brown). Immature branches — Medium green (20-I-7) with exposed branch surfaces often tinged with shades of red.

LEAVES

Size:

*Generally.*—Medium. Measurements have been taken from leaves growing on vigorous upright shoots of current season's growth.

*Average length.*—Ranges from 9.6 cm (3.780 inches) to 11.1 cm (4.370 inches) including the petiole.

*Average width.*—Ranges from 4.1 cm (1.614 inches) to 4.9 cm (1.929 inches).

Thickness: Average.

Form: Most frequently obovate, but can at times be nearly oval. The leaf apex is acute and is frequently twisted sideways.

Color:

*Upwardly disposed surface.*—Dark green (24-L-9).

*Downwardly disposed surface.*—Lighter grey-green (23-L-5 Cedar Green). Young shoot tips are a light green-yellow (18-K-5).

Marginal form:

*Generally.*—Crenate. The crenations are relatively large and coarse. Crenations are often double and at times triple especially near mid-margin.

Leaf margin: Slightly undulate.

Petiole:

*Size.*—Medium.

*Length.*—10 mm (0.3937 inches) to 11 mm (0.4330 inches).

*Thickness.*—1.0 mm (0.394 inches) to 1.5 mm (0.0591 inches).

*Color.*—Light green (18-I-5 Sky Green) to a lighter yellow-green (17-J-2). Reddish color tones are often present on and within the petiole groove.

Glands:

*Size.*—Medium.

*Number.*—From 0 to 2 glands are commonly present.

*Form.*—Somewhat intermediate in form, from oval to globose.

*Position.*—Usually borne on a short stalk.

*Pattern.*—Usually present only at the base of the leaf margin. When more than one gland is present, the glands are variable in arrangement, but are most frequently opposite.

*Color.*—Glossy light green (17-L-7 Viridine Green) when young, becoming darker and deteriorating with age.

Stipules: Most are early deciduous.

*Size.*—Small.

*Length.*—5 mm (0.1969 inches) to 6 mm (0.2392 inches).

*Form.*—Very narrow linear lanceolate with serrate margins.

*Color.*—Light green (17-I-4) when young, becoming darker with age.

FLOWERS

Flower buds: Hardy under typical San Joaquin Valley climatic conditions.

*Size.*—Medium.

*Form.*—Plump and conic.

*Position.*—Slightly appressed to the shoot.

*Scale surface.*—Glabrous.

*Color.*—Dark brown (8-J-11 Montella Brown).

Date of bloom: Mar. 2, 1993. The date of bloom is not significantly different than that of the parent "Late Santa Rosa" plum tree. The bloom is mid-range in comparison with other common commercial Japanese plum varieties.

Bloom:

*Quantity.*—Abundant. Two to four flower buds are present per node, most frequently four.

Size:

*Generally.*—Medium.

*Diameter.*—Range from 18 mm (0.7087 inches) to 22 mm (0.8661 inches) when fully open.

Pedicel: Very finely pubescent, especially basally, with very short, fine, scattered pubescence.

*Size.*—Medium.

*Length.*—10 mm (0.3937 inches) to 11 mm (0.4331 inches).

*Thickness.*—Averaging 1.0 mm (0.0394 inches).

*Color.*—Light green (20-K-4).

Petals:

*Color.*—White (1-A-1).

*Size.*—Medium.

*Length.*—9.5 mm (0.3740 inches) to 11.5 mm (0.4528 inches).

*Width.*—9.0 mm (0.3543 inches) to 10.0 mm (0.3937 inches).

*Form.*—Broadly ovate.

*Number.*—Five.

*Claw.*—Form — Truncate, relatively short and thick.

*Margin.*—Very undulate throughout and substantially cupped inwards, even at full maturity.

*Apex.*—Usually rounded.

Nectaries:

*Color.*—Brownish-orange (13-K-11 Martinique) when young, becoming slightly darker with age.

Calyx:

*Color.*—Greenish (20-K-4) basally and a brownish-green (13-K-3 Olive Sheen) over the upper calyx surface.

*Surface.*—Glabrous.

Sepals:

*Size.*—Moderately large.

*Form.*—Ovate.

*Color.*—Light green (19-J-7) with some brown shading present.

*Margin.*—Serrate and colored a light pink (2-A-8).

Anthers:

*Size.*—Medium.

*Color.*—Yellow-gold (9-L-2), both ventrally and dorsally.

Stamen:

*Color.*—White (1-A-1).

*Length.*—Varies from 6 mm (0.2362 inches) to 11 mm (0.4331 inches). The longest stamens are slightly longer than the pistil.

Pollination requirements: Self pollinating.

Pollen:

*Quantity.*—Moderate.

*Color.*—Yellow-gold (10-L-3).

Pistil:

*Surface.*—Glabrous.

*Color.*—Pale green (18-J-2).

*Length.*—Varies from 7 mm (0.2756 inches) to 8 mm (0.3150 inches), including the ovary.

FRUIT

Generally: The fruit of the "Early Rosa" plum tree requires approximately the same amount of thinning as the fruit of the "Santa Rosa" plum tree. The amount of thinning depends on weather conditions during the blooming period. Very little fruit drop has been observed.

Maturity when described: Ripe for commercial harvesting and shipment approximately June 14 to June 19 in 1992, or about seven to ten days before the "Santa Rosa" plum tree, near Le Grand in the northern San Joaquin Valley of California. Fruit as described herein is at an advanced stage of commercial maturity.

Size:

*Generally.*—Medium to large and quite uniform. The fruit of the "Early Rosa" plum tree are larger in size than the fruit of the "Santa Rosa" plum tree.

*Average diameter in the axial plane.*—53 mm (2.087 inches) to 58 mm (2.283 inches).

*Average diameter transverse in the suture plane.*—51 mm (2.008 inches) to 58 mm (2.283 inches).

*Average diameter cheek plane.*—52 mm (2.047 inches) to 57 mm (0.0884 inches).

Form:

*Uniformity.*—Ovate to cordate in lateral aspect. Globose in apical aspect.

*Symmetry.*—Usually slightly asymmetrical.

Suture:

*Generally.*—An inconspicuous thin line extends from base to apex. The suture is quite smooth and usually takes on the color of the surrounding blush coloration. At times, however, the suture can be slightly darker than the surrounding coloration.

Ventral surface:

*Generally.*—Somewhat variable. Usually this surface is quite smooth and rounded, but at times a small amount of lipping can be present.

Stem cavity:

*Generally.*—Small.

*Width.*—Ranges from 18 mm (0.7087 inches) to 20 mm (0.7874 inches).

*Depth.*—Moderately deep. 12 mm (0.4724 inches) to 13 mm (0.5118 inches).

*Length.*—18 mm (0.7087 inches) to 21 mm (0.8268 inches).

*Form.*—From globose to slightly oval.

Stem:

*Length.*—Medium. 13 mm (0.5118 inches) to 16 mm (0.6300 inches).

*Thickness.*—Relatively thick, averaging 2.0 mm (0.0787 inches).

*Color.*—Ranges from a medium green (20-K-6 Piquant Green) to a mixed green and brown (14-J-6).

Base:

*Form.*—Variable from generally rounded to very slightly truncate.

*Angle.*—Variable from slightly oblique to nearly at right angle to the fruit axis.

Apex:

*Form.*—Rounded to slightly raised.

Pistil point: Small with a small callous spot and variable but is most frequently slightly oblique.

Skin:

*Thickness.*—Medium. Tenacious to flesh at commercial maturity.

*Texture.*—Glabrous.

*Tendency to crack.*—No observed tendency to crack.

*Flavor.*—Acidic.

*Blush color.*—The skin is usually 100 percent blush colored at full maturity. Ranges from a bright cherry red (4-L-10 Holly Berry Red) to a dark purple (8-H-6 Granada). Numerous small light colored dots are present over the fruit surface, especially over the apical shoulders and laterally.

*Ground color.*—At full maturity, usually no ground coloration is visible.

*Flesh color.*—At full maturity the interior flesh color is light red (1-F-11 Tiger Lily) to a light amber-yellow (10-J-7 Mirabelle Yellow) with much variation in shading occurring between fruit samples and also within an individual fruit. The flesh is more red (3-K-11 Flash Red) in color from 6 mm (0.2362 inches) to 7 mm (0.2756 inches) under the skin and within 5 mm (0.1969 inches) to 6 mm (0.2362 inches) around the stone. Many light colored medium length fibers are present throughout the flesh.

*Juice production.*—Juicy.

*Flavor.*—Sweet, rich flavor. The skin and flesh area next to the stone are acidic.

*Aroma.*—Moderately aromatic with a pleasant, sweet aroma.

*Texture.*—Moderately firm at commercial maturity, becoming juicy with after-ripening.

*Ripening.*—Even.

*Eating quality.*—Excellent.

Stone:

*Attachment.*—Clingstone.

*Fibers.*—Numbers — Many are attached to the stone, both laterally and along both dorsal and ventral sutures. Length — Medium.

*Size.*—Medium. Length— Ranges from 23 mm (0.9055 inches) to 25 mm (0.9843 inches). Width — 17 mm (0.6693 inches) to 18 mm (0.7087 inches). Thickness — 9 mm (0.3543 inches) to 10 mm (0.3937 inches).

*Form.*—Generally — Somewhat irregular, from oval to ovate.

*Apex.*—Shape — Slightly raised, irregular and slightly eroded.

*Color.*—Dry — Light chamois-buff (10-G-3 Cornsilk).

*Base.*—Shape — Variable in form, but most frequently truncate. The base is usually oblique to the stone axis.

*Sides.*—Generally — Usually equal or nearly so.

*Hilium.*—Form — Irregular oval. The hilium area is heavily eroded. Size — Small.

*Surface.*—The lateral surfaces of the stone are slightly roughened with basal grooves and ridges converging basally. A moderately deep groove is present laterally, extending longitudinally from base to apex and roughly parallel to the ventral suture but from 3 mm (0.1181 inches) to 4 mm (0.1575 inches) below the suture edge.

*Ventral suture.*—Generally rounded and narrow with an irregular and slightly jagged edge. A prominent wing is at times evident basally.

*Dorsal edge.*—Medium in width with a deep groove from base to apex and wider basally. The groove narrows over the apical shoulder and at times is discontinuous in this area. The dorsal groove is suspended by two narrow, somewhat notched and jagged ridges.

*Tendency to split.*—No tendency of the stones to split has been observed.

Although the new variety of plum tree possesses the described characteristics noted above as a result of the growing conditions prevailing near Le Grand in the northern San Joaquin Valley of California, it is to be understood that variations of the usual magnitude and characteristics incident to changes in growing conditions, irrigation, fertilization, pruning, pest control, seasonal climatic variation and the like are to be expected.

Having thus described and illustrated my new variety of plum tree, what I claim as new and desire to be secured by Plant Letters Patent is:

1. A new and distinct variety of plum tree substantially as illustrated and described which is somewhat remotely similar to the "Santa Rosa" plum tree (unpatented), but from which it is distinguished by producing fruit which are mature for commercial harvesting and shipment approximately June 14 to June 19, or about seven to ten days before the "Santa Rosa" plum tree, in the northern San Joaquin Valley of California and which has a bright cherry red to dark purple skin coloration.

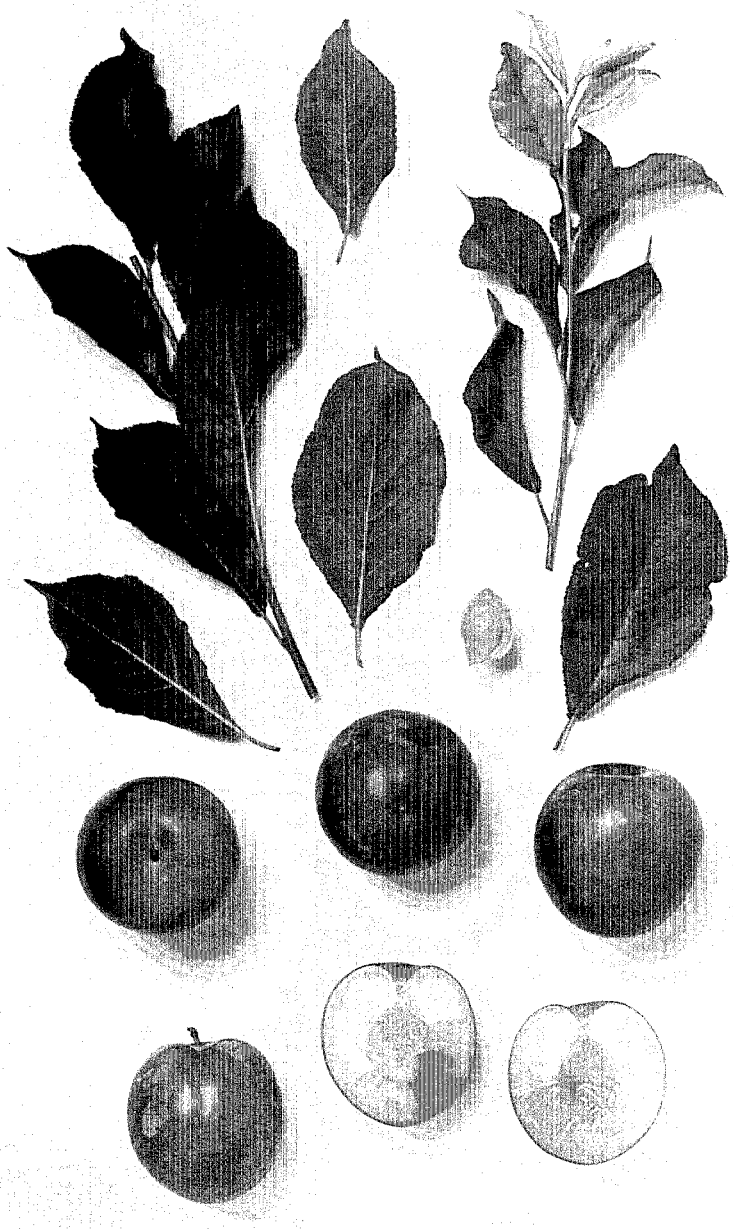

* * * * *